(12) United States Patent
Carmi et al.

(10) Patent No.: US 11,419,717 B2
(45) Date of Patent: Aug. 23, 2022

(54) INTRALUMINAL SUPPORT STRUCTURE AND PROSTHETIC VALVE FOR THE SAME

(71) Applicant: Open Stent Solution SAS, Dury (FR)

(72) Inventors: Doron Carmi, Ramat Hasharon (IL); Eitan Berger, Kadesh Barnea (IL)

(73) Assignee: Open Stent Solution SAS, Dury (FR)

( * ) Notice: Subject to any disclaimer, the term of this patent is extended or adjusted under 35 U.S.C. 154(b) by 0 days.

(21) Appl. No.: 16/627,316

(22) PCT Filed: Jun. 26, 2018

(86) PCT No.: PCT/IL2018/050698
§ 371 (c)(1),
(2) Date: Dec. 29, 2019

(87) PCT Pub. No.: WO2019/003221
PCT Pub. Date: Jan. 3, 2019

(65) Prior Publication Data
US 2020/0163759 A1    May 28, 2020

Related U.S. Application Data

(60) Provisional application No. 62/526,693, filed on Jun. 29, 2017.

(51) Int. Cl.
*A61F 2/06* (2013.01)
*A61F 2/91* (2013.01)
(Continued)

(52) U.S. Cl.
CPC .......... *A61F 2/2418* (2013.01); *A61F 2/2436* (2013.01); *A61F 2/844* (2013.01); *A61F 2002/91591* (2013.01); *A61F 2210/0014* (2013.01); *A61F 2230/0006* (2013.01); *A61F 2230/008* (2013.01);
(Continued)

(58) Field of Classification Search
CPC ........ A61F 2/06; A61F 2/2418; A61F 2/2436; A61F 2/844; A61F 2002/91591; A61F 2210/0014; A61F 2230/0006; A61F 2230/0017; A61F 2230/0067;
(Continued)

(56) References Cited

U.S. PATENT DOCUMENTS

| 4,771,773 A | 9/1988 | Kropf |
| 5,007,926 A * | 4/1991 | Derbyshire ............... A61F 2/92 606/191 |

(Continued)

FOREIGN PATENT DOCUMENTS

| EP | 0997115 B1 | 10/2003 |
| EP | 1830744 A2 | 9/2007 |

(Continued)

OTHER PUBLICATIONS

EP18822634.4 Extended Search Report dated Feb. 24, 2021.
(Continued)

*Primary Examiner* — Ann Schillinger
(74) *Attorney, Agent, or Firm* — Wilson Sonsini Goodrich & Rosati

(57) ABSTRACT

An intraluminal support structure having a delivery configuration that is a crimped open configuration to increase flexibility while maneuvering in the anatomy and having a small scarring signature.

29 Claims, 9 Drawing Sheets

(51) Int. Cl.
*A61F 2/24* (2006.01)
*A61F 2/844* (2013.01)
*A61F 2/915* (2013.01)

(52) U.S. Cl.
CPC ............... *A61F 2230/0017* (2013.01); *A61F 2230/0067* (2013.01); *A61F 2230/0076* (2013.01); *A61F 2230/0078* (2013.01); *A61F 2250/0067* (2013.01)

(58) Field of Classification Search
CPC ...... A61F 2230/0076; A61F 2230/0078; A61F 2230/008; A61F 2250/0067; A61F 2/91
See application file for complete search history.

(56) References Cited

U.S. PATENT DOCUMENTS

| | | | |
|---|---|---|---|
| 5,147,387 A | 9/1992 | Jansen et al. | |
| 5,405,379 A | 4/1995 | Lane | |
| 5,411,552 A | 5/1995 | Andersen et al. | |
| 5,441,515 A | 8/1995 | Khosravi et al. | |
| 5,443,500 A | 8/1995 | Sigwart | |
| 5,824,053 A | 10/1998 | Khosravi et al. | |
| 5,836,964 A * | 11/1998 | Richter | A61F 2/91 606/194 |
| 5,925,063 A | 7/1999 | Khosravi | |
| 6,451,025 B1 | 9/2002 | Jervis | |
| 6,540,777 B2 | 4/2003 | Stenzel | |
| 7,011,674 B2 | 3/2006 | Brenneman | |
| 7,374,571 B2 | 5/2008 | Pease et al. | |
| 7,637,937 B2 * | 12/2009 | Case | A61F 2/90 623/1.15 |
| 7,780,724 B2 | 8/2010 | Kheradvar et al. | |
| 8,277,500 B2 * | 10/2012 | Schmid | A61F 2/82 623/1.15 |
| 8,382,822 B2 * | 2/2013 | Pavcnik | A61F 2/2475 623/2.14 |
| 9,402,720 B2 | 8/2016 | Richter et al. | |
| 9,505,562 B2 | 11/2016 | Petrovic | |
| 9,707,108 B2 * | 7/2017 | Davis | A61F 2/82 |
| 9,907,681 B2 | 3/2018 | Tobis et al. | |
| 10,517,718 B2 | 12/2019 | Richter et al. | |
| 2002/0077693 A1 * | 6/2002 | Barclay | A61L 31/048 623/1.13 |
| 2005/0125053 A1 * | 6/2005 | Yachia | A61F 2/915 623/1.15 |
| 2007/0156158 A1 * | 7/2007 | Herzberg | A61B 17/1146 606/152 |
| 2008/0183273 A1 * | 7/2008 | Mesana | A61F 2/2433 623/1.11 |
| 2010/0152839 A1 | 6/2010 | Shandas et al. | |
| 2010/0185275 A1 | 7/2010 | Richter et al. | |
| 2011/0172784 A1 * | 7/2011 | Richter | A61F 2/844 623/23.68 |
| 2011/0238168 A1 | 9/2011 | Pellegrini et al. | |
| 2013/0053943 A1 | 2/2013 | Denison et al. | |
| 2014/0128962 A1 * | 5/2014 | Tippett | A61F 2/86 623/1.16 |
| 2016/0022448 A1 | 1/2016 | Tobis et al. | |
| 2017/0065411 A1 * | 3/2017 | Grundeman | A61F 2/2412 |
| 2017/0128203 A1 | 5/2017 | Zhang et al. | |
| 2018/0214263 A1 * | 8/2018 | Rolando | A61F 2/2415 |
| 2018/0256321 A1 | 9/2018 | Zhang et al. | |
| 2018/0256322 A1 | 9/2018 | Zhang et al. | |
| 2018/0263768 A1 | 9/2018 | Zhang et al. | |
| 2019/0209312 A1 | 7/2019 | Zhang et al. | |
| 2019/0209315 A1 | 7/2019 | Zhang et al. | |
| 2019/0209316 A1 | 7/2019 | Zhang et al. | |

FOREIGN PATENT DOCUMENTS

| | | |
|---|---|---|
| EP | 2529706 A1 | 12/2012 |
| EP | 2877124 A2 | 6/2015 |
| WO | WO-9915224 A1 | 4/1999 |
| WO | WO-2010079427 A1 | 7/2010 |
| WO | WO-2016178126 A1 | 11/2016 |
| WO | WO-2017061956 A1 | 4/2017 |
| WO | WO-2018150392 A1 | 8/2018 |
| WO | WO-2019003221 A1 | 1/2019 |
| WO | WO-2020214096 A1 | 10/2020 |

OTHER PUBLICATIONS

PCT/IL2018/050698 International Search Report and Written Opinion of the International Searching Authority dated Oct. 18, 2018.

* cited by examiner

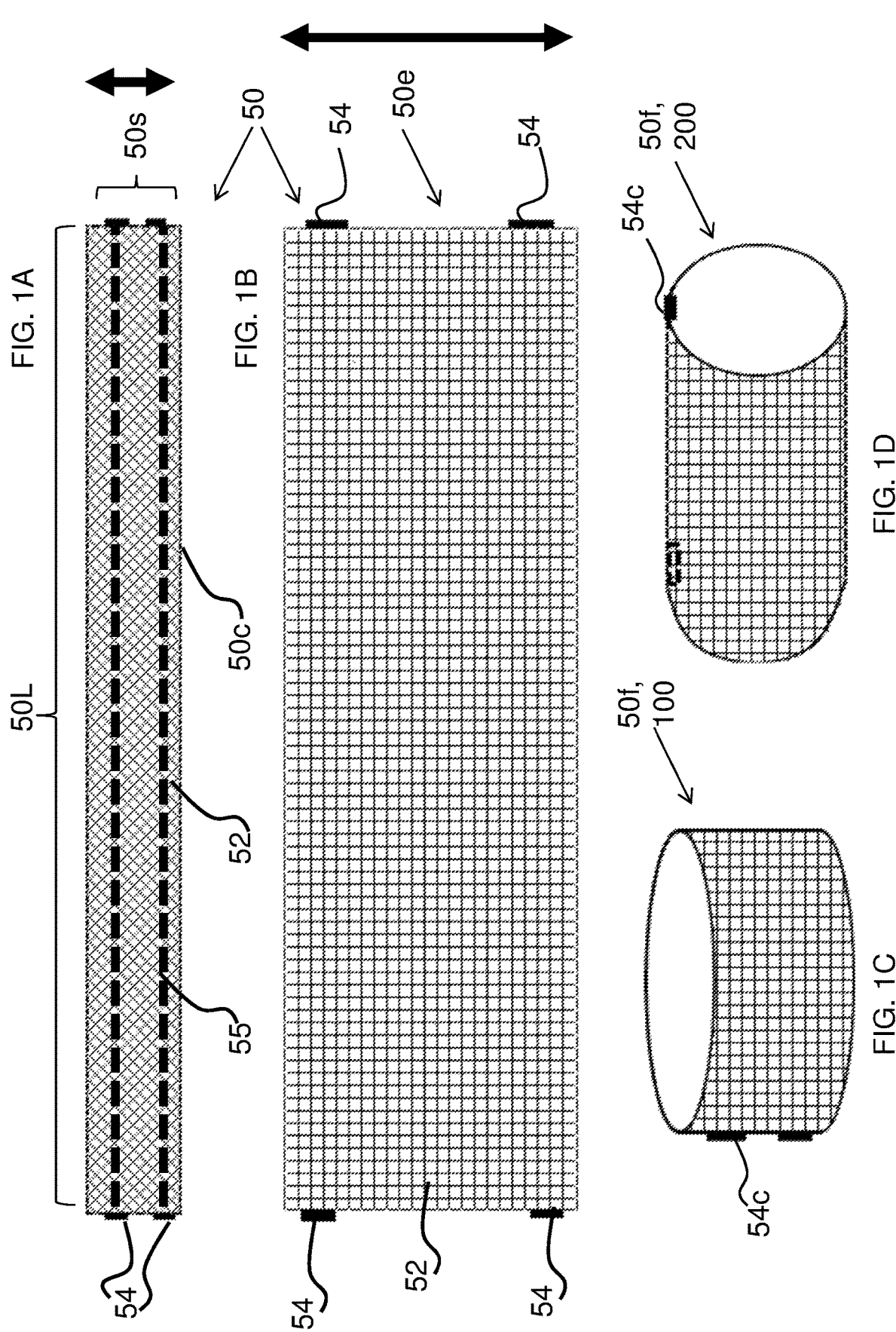

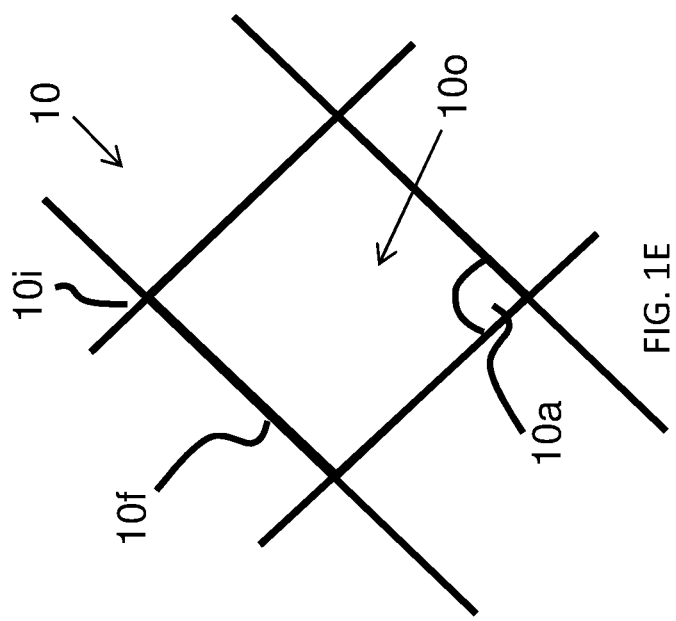
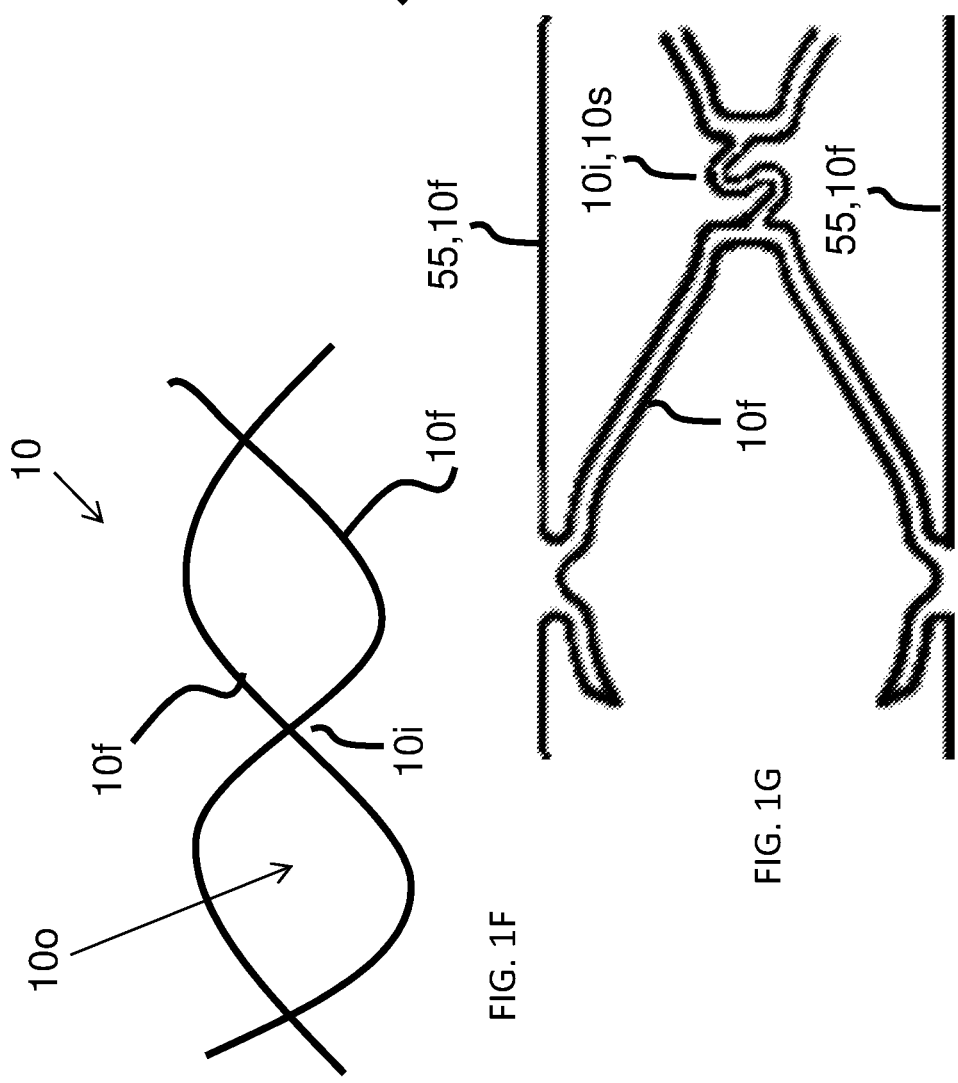

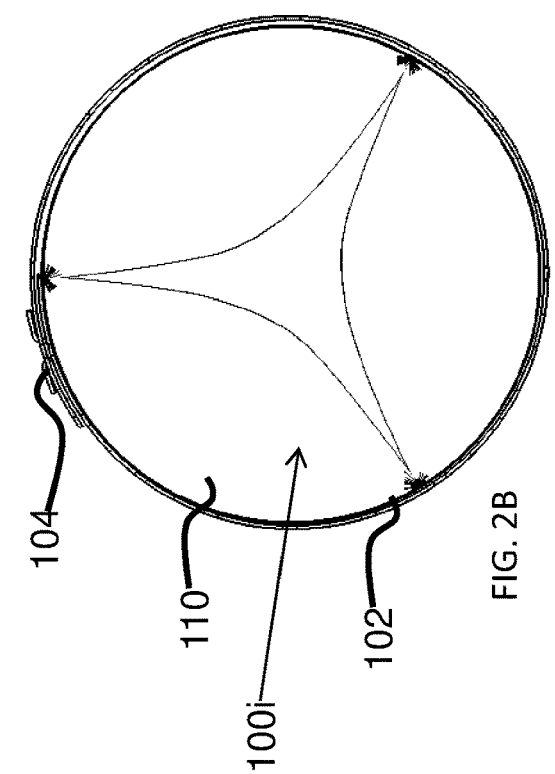
FIG. 2A
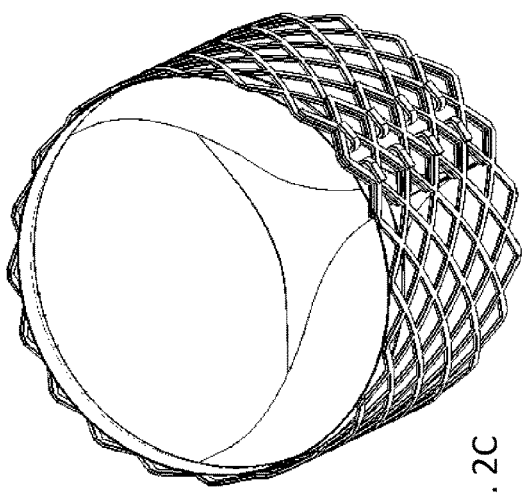
FIG. 2B
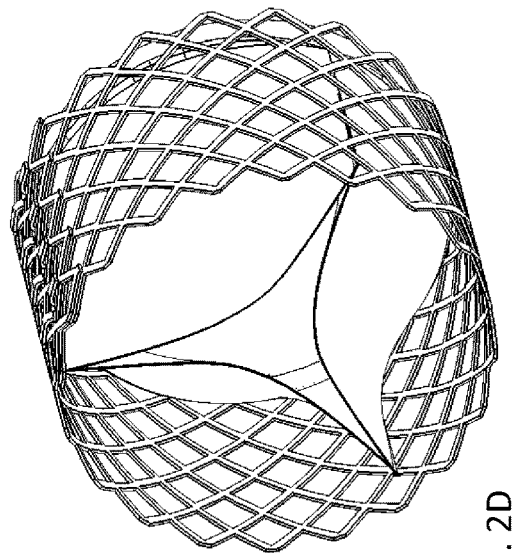
FIG. 2C
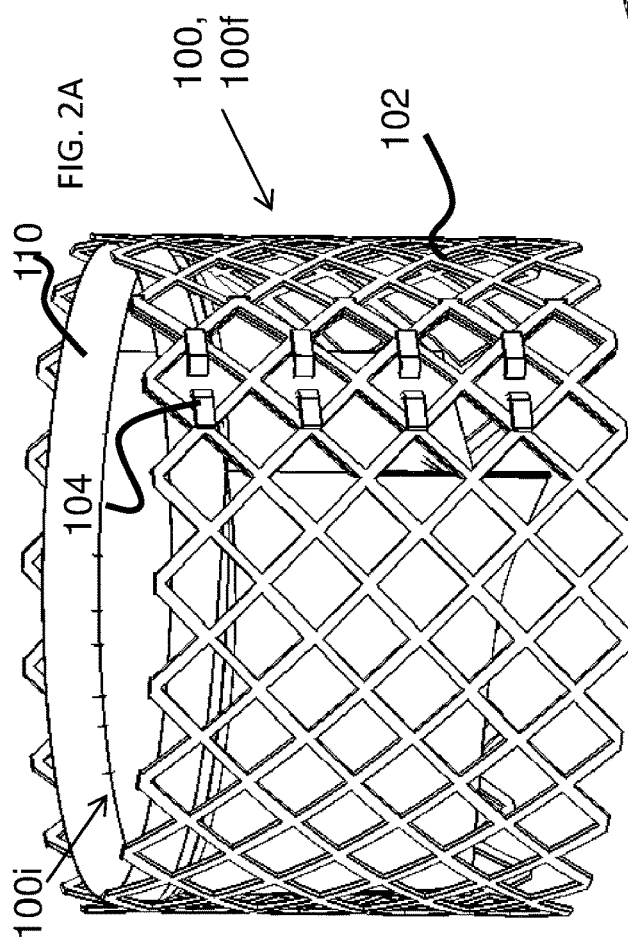
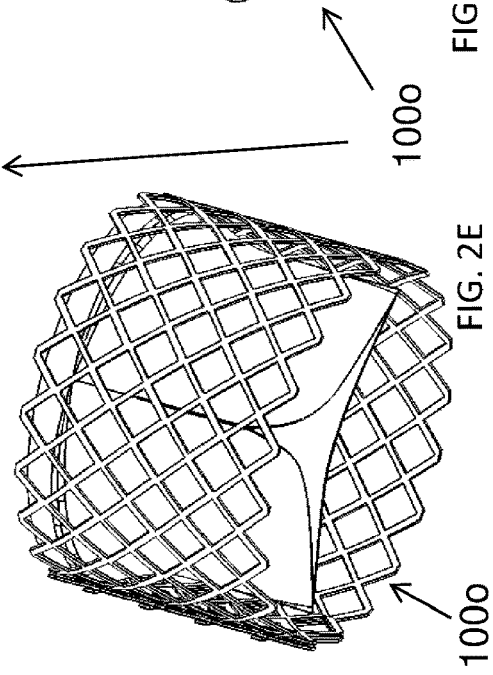
FIG. 2E
FIG. 2D

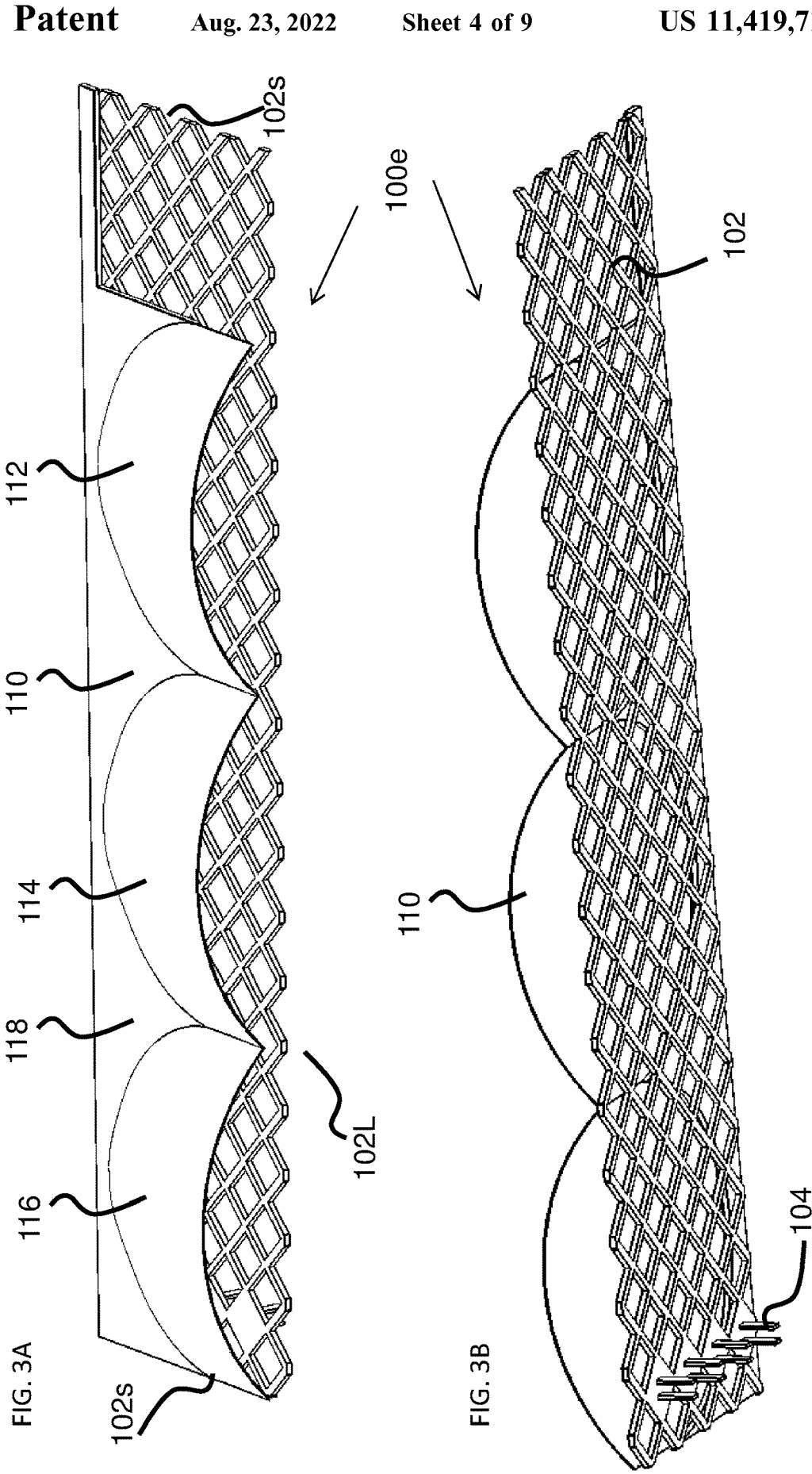

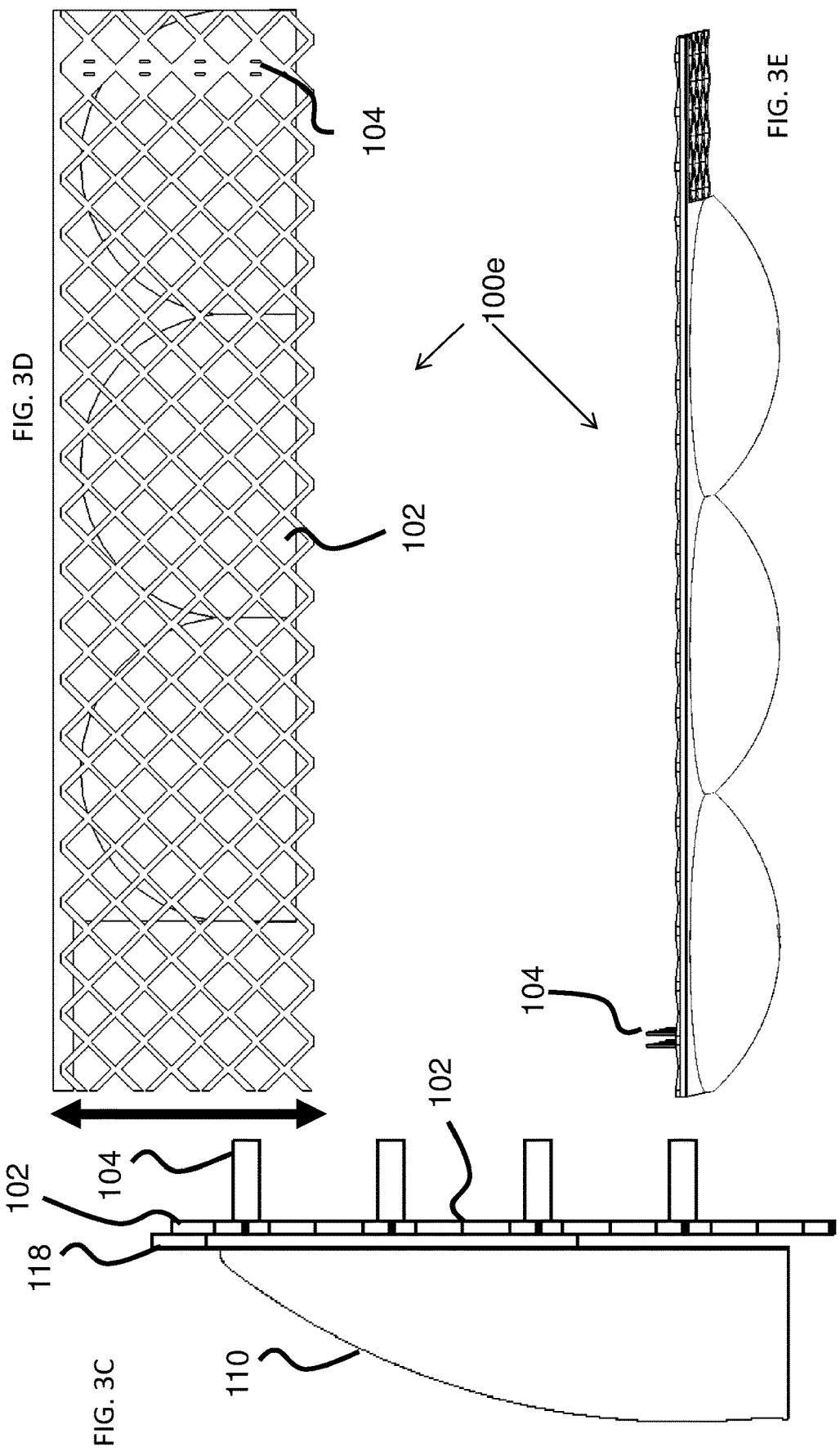

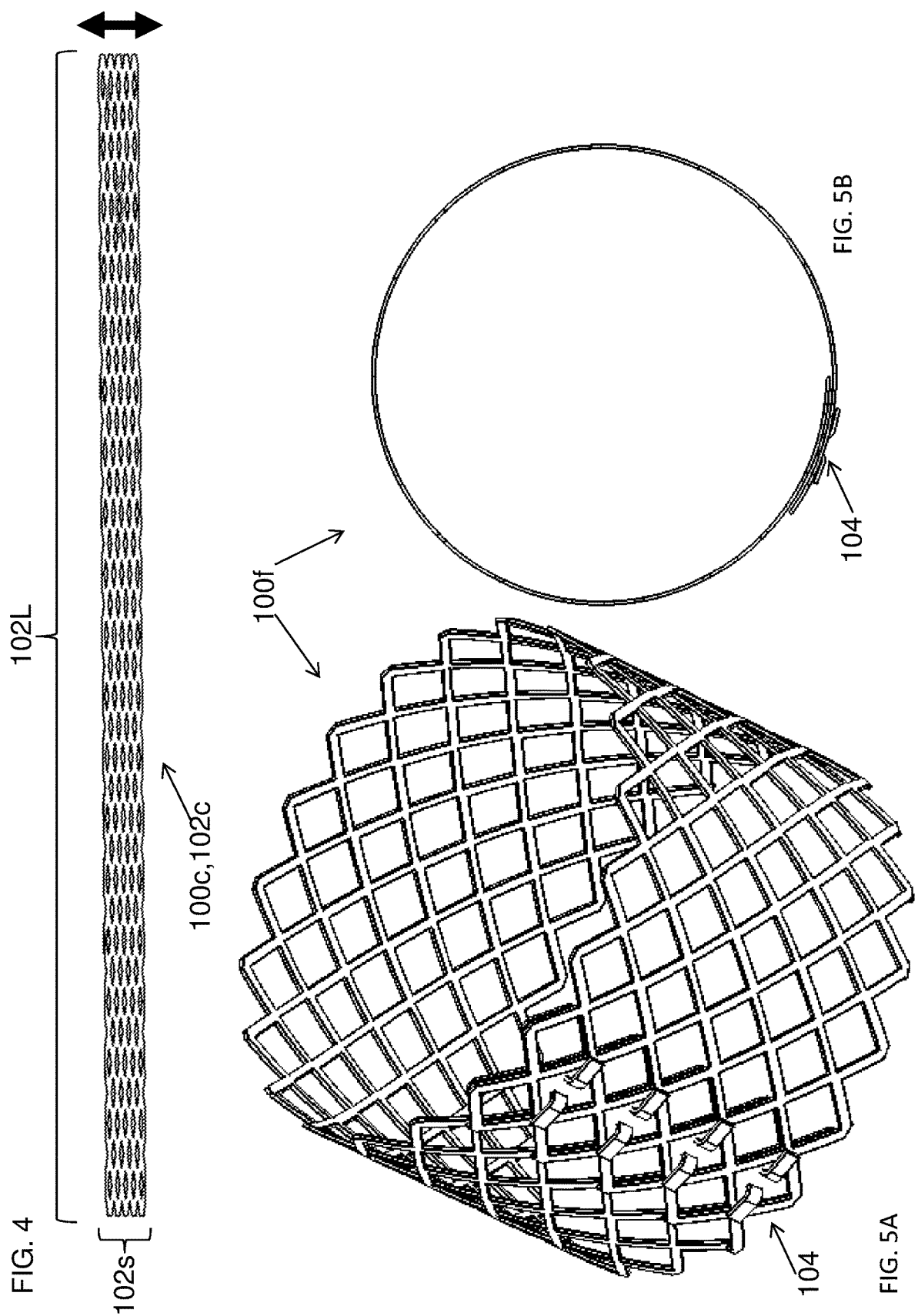

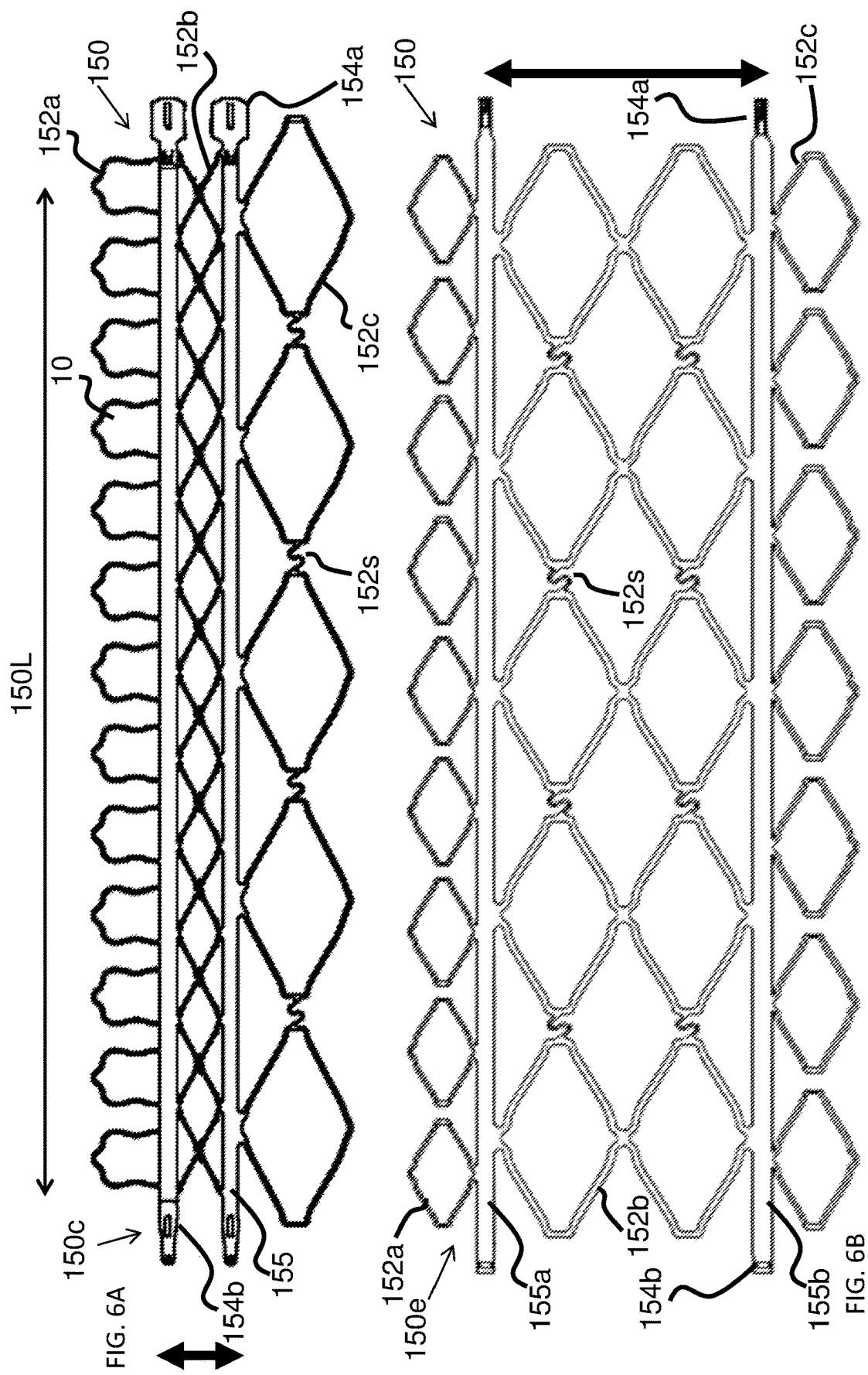

INTRALUMINAL SUPPORT STRUCTURE AND PROSTHETIC VALVE FOR THE SAME

FIELD OF THE INVENTION

The present invention relates to an intraluminal support structure device, system and a method for delivery of the same in a trans-catheter method, and in particular, to such an intraluminal support structure that is delivered in a crimped open configuration and is transitioned to a final folded and closed configuration during deployment within the anatomy.

BACKGROUND OF THE INVENTION

Across the globe Heart Valve Disease (HVD) affects many people globally. HVD manifests in abnormal valve leaflet tissue in various ways including excess tissue growth, tissue degradation, tissue rupture, tissue hardening, tissue calcification, abnormal tissue re-positioning in response to cardiac configuration during different stages of the cardiac cycle, for example annular dilation or ventricular reshaping. Such tissue deformation leads degrading valve function for example leakage, backflow as a result of valve insufficiency, resistance to blood forward flow as a result of valve stenosis.

In such situations the best treatment mode is generally placement of a trans-catheter valve prosthesis. A prosthetic valve generally provides a functional replacement of a damaged heart valve. In recent years the preferred mode of delivery of placement of a prosthetic valve has been via catheterization techniques.

U.S. Pat. No. 4,733,665 to Palmaz discloses a wire mesh tube vascular graft (stent) that is expanded within a blood vessel by an angioplasty balloon associated with a catheter for repairing blood vessels narrowed or occluded by disease.

U.S. Pat. No. 5,836,964 to Richter et al, discloses a method for fabricating as cylindrical stent from sheet metal from the manufacture process and up to before delivery in patient.

U.S. Pat. No. 5,441,515 to Khosravi et al, discloses an intravascular stent comprising a cylindrical sheet having overlapping edges that interlock. The edges have a series of protrusions and apertures that interlock and ratchet as the stent expands to an open position to support a section of arterial wall. The interlocking mechanism used to ensure the stent's patency while imparting some flexibility to the stent.

U.S. Pat. No. 5,411,552 to Anderesen et al, disclose a method for implantation of a valve prosthesis via balloon catheterization techniques making it possible to insert a cardiac valve prosthesis without an invasive surgical procedure including opening the thoracic cavity.

U.S. Pat. No. 6,540,777 to Stenzel describes a locking stent having at least one lockable cell which includes a first locking member and a second locking member that are interlocked to impart increased scaffolding strength to the stent.

A stent is typically delivered in an unexpanded state to a desired location in a bodily lumen and then expanded. The stent may be expanded via the use of mechanical device such as a balloon or the stent may be self-expanding.

SUMMARY OF THE INVENTION

Trans-catheter therapies for structural heart diseases raised the need for the delivery of large devices through native vessels, cardiac walls and the cardiac septum. However, radial crimping of these devices, as provided by the state of the art devices, creates a rigid and relatively large stem inside the device's delivery sheath. These limitations, both in rigidity and size, result in the limited movement and maneuverability during the procedure. In particular it is difficult to maneuver the device in acute angles during the procedure.

Furthermore, the large size (diameter) of the state of the art device further leave large orifices in the cardiac septum at the end of the procedure.

In the actual state of art, all the devices are crimped and deployed in a radial manner, which means that currently there isn't any available option to deliver such devices without significant septum damage and further lead to significant maneuverability limitation.

There is an unmet need for, and it would be highly useful to have, a stent that is more flexible in its crimped state so as to facilitate delivery in any anatomy and to allow for easier maneuverability through the tortuous anatomy. Accordingly, increased stent flexibility greatly increases the capability of delivery and deployment of stents.

While flexibility is important stents must also exhibit high scaffolding in the expanded and/or non-crimped state so as to increase the stability of the stent within the delivery site.

This dual need for flexibility in the crimped state and high scaffolding in the expanded (non-crimped) state presents an unsolved problem in the art as the two characteristics are inversely proportional. Specifically, as stent flexibility is increased, scaffolding is decreased and similarly, as scaffolding is increased, flexibility is decreased. Accordingly, there remains a need for a stent having a high degree of flexibility in the crimped low profile state and high scaffolding in the expanded final state.

The prior art discloses cylindrical stents that are convenient for catheterization delivery in that they can assume a small diameter and can be readily expanded with a balloon or alternatively may be configured to be self-expanding. However, due to the cylindrical configuration of stents there is an inherent structural limitation in the level of available flexibility, especially of larger stents configured to form valve prosthesis.

Trans-catheter delivery solution for the treatment of valvular disease wherein, valve replacement is provided by way of catheter facilitated delivery, has further raised the need to deliver a relatively large stents integrated with its biological component, forming a prosthetic valve. Prosthetic valves are introduced to the cardiac anatomy through native vessels, cardiac walls and septum. Accordingly, large stents forming a valve prosthesis, for the purpose of valve delivery, require a high degree of flexibility to facilitate the catheter delivery process.

To this end, state of the art stents are difficult to maneuver within the delivery catheter because of their length and relatively large diameter makes them difficult to maneuver in the tortuous anatomy. Furthermore, the large stent diameter, when in crimped or low profile configures, makes it difficult for the required maneuverability. Specifically establishing acute angels during the delivery is currently not possible with state of the art prosthetic valves, due to the diameter of the cylindrical stent. Furthermore, during trans-catheter delivery the prosthetic valve stent is introduced through the cardiac septum. Current large diameter stent disadvantageously leave a large orifice in the cardiac septum.

Accordingly it would be advantageous to have a stent capable of increased flexibility while maintaining minimal dimensions in the crimped/small configuration.

Embodiments of the present invention provide a stent having a planar configuration utilized during the delivery phase wherein the support structures assumes a low profile crimped open configuration. The planar stent is configured to assume a final closed folded configuration during deployment at the tissue targeted site.

In embodiments the planar stent may be fit with a valve prosthesis to form a valve prosthesis that may be delivered by transcatheterization.

In one embodiment, the invention is directed to stents comprising a plurality of interconnected cells where at least one of the interconnected cells is a lockable cell. The lockable cell includes a first locking member and a second locking member disposed opposite the first member. The first and second locking members are movable between a first position in which they do not lock with one another to a position in which they lock with one another.

Within the context of this application the term "open crimped configuration" substantially refers to a crimped small profile configuration of the support structure in its delivery state that is to be delivered to an implantation site with a delivery tool such as a catheter. The term "open" refers to a non-tubular or non-cylindrical structure, for example such as a stent or valve. Therein the term "open crimped configuration" refers to a non-radially crimped support structure.

Within the context of this application the term "open non-crimped planar configuration" substantially refers to a configuration of the support structure in its flat planar and preferably single layer configuration having maximal dimension prior to being crimped. The term "open" refers to a non-tubular or non-cylindrical structure, for example such as a stent or valve.

Within the context of this application the term "open" in reference to a configuration of the support structure refers to a non-tubular or non-cylindrical structure, for example such as a stent or valve. The term "open" may be utilized to interchangeably refer to a single layer planar structure that is substantially flat or to a multilayered planar structure that is substantially flat.

Within the context of this application the term closed non-planar folded configuration refers to the final support structure configuration as would be placed within the anatomy, for example in the form of a tubular stent and/or cylindrical valve. The closed configuration therefore refers to the final shape and/or state of the vessel support structure following its transformation.

In embodiments of the present invention provides an intraluminal support structure, for example a stent and/or prosthetic valve, having a body capable of transitioning between three configuration including, an open non-crimped planar configuration having a long axis and a short axis, an open crimped configuration and a closed non-planar folded configuration;

The support structure characterized in that the open non-crimped planar configuration is crimped along the long axis to transition the body to form the open crimped configuration and providing the body with a minimal short axis and a maximal long axis therein providing the open crimped configuration with increased flexibility.

In embodiments the open crimped configuration is associated with a delivery carrier member in the form of a catheter or sheath defining a delivery system; the delivery system is utilized for introducing the support structure to a body for implantation at a delivery site or implantation site; and wherein the open crimped configuration is controllably disassociated from the delivery system to be deployed at the delivery site, and wherein during deployment the open crimped configuration transitions to assume the closed non-planar folded configuration, wherein the transition is established by way of at least one of expansion, torsion or folding and wherein the closed non-planar folded configuration is finalized by closing the body by interlocking an end thereof along one of the long axis or the short axis.

In embodiments the closed non-planar folded configuration may be closed by overlapping and interlocking portions of the body along one of the long axis or the short axis.

In embodiments the support structure body may be provided from an arrangement of a plurality of filaments forming a planar scaffold, and wherein the filaments form a interlinking points defining an interlinking angle at the interlinking point that define a planar opening formed from at least two opposing interlinking points, characterized in that the support structure is configured to transition between the open non-crimped planar configuration to the crimped configuration by adjusting the interlinking angle.

In embodiments the support structure body may further comprises at least one axial support member along at least a portion of the length of the body along the long axis. In embodiments the axial support member is disposed between two opposing long edges of the long axis. In embodiments the support structure may comprise at least two axial support members forming an upper portion, medial portion, and lower portion along the support structure body.

In embodiments the axial support member is provided form of a continuous flexible sheet.

In embodiments the length of the short axis may be reduced by at least 20% and up to about 80% when transitioning between the open non-crimped planar configuration and the crimped configuration.

In embodiments the length of the long axis increases by a factor of up to about 100% when transitioning between the open non-crimped planar configuration and the open crimped configuration.

In embodiments the support structure may further comprises a valve body defining a prosthetic valve. In embodiment the valve body is configured to form a prosthetic valve in the form for example including but not limited to: semilunar valve, pulmonary valve, aortic valve, atrioventricular valve (AV valve), mitral valve, bicuspid valve, tricuspid valve, sphincter, cervix, the like or any combination thereof.

In embodiments the valve body may be provided from optional materials for example including but not limited to biological tissue, biological matter, engineered materials, grown materials, transplanted tissue, biocompatible polymeric materials, the like and any combination thereof.

In embodiments the support structure may be coated with at least one or more selected from the group consisting of an agent, a medicament, a drug, an eluting medicament, a controlled release medicament, a controlled release agent, any combination thereof.

In embodiments the present invention provides a method for delivering an intraluminal support structure having a body capable of transitioning between three configuration including, an open non-crimped planar configuration having a long axis and a short axis, an open crimped configuration and a closed non-planar folded configuration; the support structure characterized in that the open non-crimped planar configuration is crimped along the long axis to transition the body to form the open crimped configuration and providing the body with a minimal short axis and a maximal long axis therein providing the open crimped configuration with increased flexibility, the method comprising:

mounting the support structure in the crimped configuration on a distal end of a delivery catheter for intraluminal delivery through a body lumen therein defining a loaded catheter ready for introduction into the body;

introducing the catheter into the body and advancing the loaded catheter through the body lumen and anatomical tissue until reaching the delivery site (implantation site);

deploying the support structure in the delivery site by extracting the crimped support structure from the catheter and allowing the crimped planar support structure to transition by way of expanding and folding as it is extracted from catheter so as to assume a non-planar folded configuration and closing the non-planar folded configuration by interlocking corresponding locking members so as to assume the final closed non-planar folded configuration; maneuvering the closed non-planar folded support structure to its final implanted location; and withdrawing the catheter from the body lumen.

In some embodiments the method may further comprise the stage of radially expanding the non-planar folded support structure to assume its implanted diameter. Optionally radial expanding is provided in a gradual manner including at least two individual radial expanding processes.

In some embodiments the method may further comprise suturing at least a portion of the closed non-planar folded support structure configuration onto a valve annulus.

In embodiments transitioning may be provided by way of exposing the support structure to a transitioning triggering agent or signal. Optionally the triggering agent may be selected from at least one or more from the group consisting of: exposure to a temperature change, exposure to a temperature increase, exposure to a temperature decrease, exposure to a chemical agent, exposure to an electromagnetic field, exposure to an electromagnetic current, exposure to an acoustic signal, exposure to an optical signal, exposure to an magnetic field, and any combination thereof.

In some embodiments the method may further comprise delivering at least two or more crimped planar support structures to the delivery site and coupling the two or more support structures within the delivery site to form a complex non-planar folded support structure configuration made of two or more crimped planar support structures.

In embodiments of the present invention comprises a delivery system for delivering and deploying the support structure according to embodiments of the present invention, as described above, wherein the delivery system comprises a catheter or sheath capable of receiving the support structure in the crimped configuration and wherein the folded configuration may be of any diameter or size.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

While the present description and figures depict a three leaflet valve, however embodiments of the present invention are not limited to such a valve configuration and may be accordingly be configured to form any valve type with any number of leaflets.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A-D show schematic box diagrams illustrating various views of embodiments of the present invention for an intraluminal support structure; FIG. 1A showing a planar crimped configuration; FIG. 1B showing a planar un-crimped configuration; FIG. 1C showing a long axis folded configuration; FIG. 1D showing a short axis folded configuration;

FIG. 1E-G show schematic illustration of a close up views of optional basic unit structures 10 utilized to form the support structure 50 according to embodiments of the present invention;

FIG. 2A-E show various views of an illustrative schematic diagram of the prosthetic valve assembly in its final post-delivery configuration once placed at the implantation site according to embodiments of the present invention;

FIG. 3A-E show various views of an illustrative schematic diagram of the prosthetic valve in the open non-crimped planar configuration according to embodiments of the present invention;

FIG. 4 show a perspective view of an illustrative schematic diagram of the prosthetic valve support structure in the open crimped configuration according to embodiments of the present invention;

FIG. 5A-B show various view of an illustrative schematic diagram of a support structure in the folded final configuration according to embodiment of the present invention.

FIG. 6A-D show various views of an illustrative schematic diagram of a prosthetic valve assembly according to embodiments of the present invention; FIG. 6A shows an open crimped configuration; FIG. 6B shows a non-crimped planar configuration; FIG. 6C shows a partially folded configuration; FIG. 6D shows a close up schematic view of optional locking members utilized to closed the folded configuration of the support structure of the present invention.

DESCRIPTION OF THE PREFERRED EMBODIMENTS

Figure 6D:
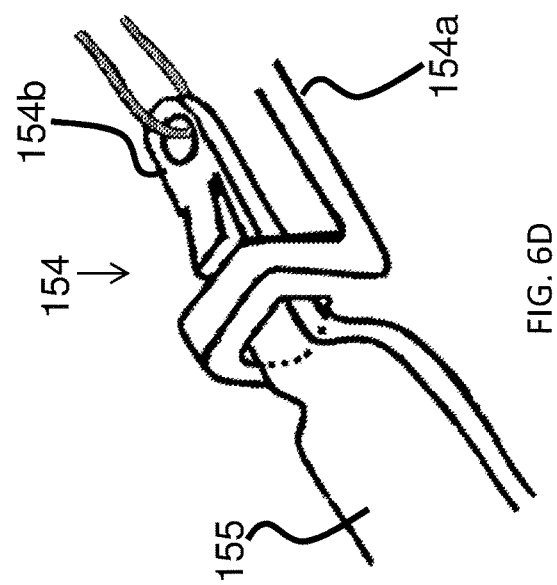

The present invention is for a vessel support structure, such as a stent or valve that is delivered to an implantation site in a crimped planar configuration so as to provide greater flexibility when maneuvering the support structure through the anatomy while leaving a small scarring signature.

The vessel support structure according to the present invention may be further configured to provide a valve support structure forming a prosthetic valve.

The vessel support structure of the present invention is configured to be introduced into the body in a crimped planar configuration during delivery and until it reaches its implantation site. Once at the implantation site the support structure is deployed from a delivery sheath wherein the support structure gradually expands to assume its final folded configuration. During deployment the open crimped support structure is configured to transition from its small open crimped delivery configuration to assume its final folded shape so as to assume a vessel support structure configuration that may be utilized as vessel support for example in the form of a stent or a prosthetic valve.

In embodiments the final shape of the vessel support structure may be configured to assume any structural geometric shape, folded shape, open folded shape, closed folded shape for example including but not limited to cylindrical, bifurcated, furcated, trapezoidal cylinder, curvilinear, tertiary structure, secondary structure helical, double helix, looped, lobular, ellipsoid, ovoid, paraboloid, vortex, hyperboloid, hyperbola, parabola, conical section, toroidal, sigmoidal, multi-loop, solenoidal, any combination thereof or the like.

The open crimped configuration utilized during delivery provides both flexibility and maneuverability while assuming a small dimension. In particular the open crimped configuration allows a practitioner to maneuver within complicated anatomy and more readily allows the device to assume acute angles, not readily possible with state of the art devices.

In some embodiments the open crimped vessel support structure may be further fit with at least a portion of a valve anatomy, for example at least two or more valve leaflets, so as to allow formation of a prosthetic valve having at least two or more leaflets in the folded final configuration. Preferably portions of the valve anatomy fit onto the vessel support structure are similarly capable of assuming a small profile and/or crimped configuration allowing the open crimped vessel support structure to retain its flexibility and maneuverability.

In embodiments the prosthetic valve may for example be configured to form a prosthetic valve of the human or animal body in any anatomical structure, organ, or form of a valve; for example including but not limited to semilunar valve, pulmonary valve, aortic valve, atrioventricular valve (AV valve), mitral valve, bicuspid valve, tricuspid valve, sphincter, cervix, or the like.

In embodiments the final structural configuration of the anatomical support structure may be composed of a plurality of support structures that may be interlinked, intertwined, coupled and/or associated with one another during the implantation and/or deployment process so as to form a final structural configuration of the support structure. For example, two or more support structures may be delivered to an implantation site substantially simultaneously and/or sequentially in order to allow them to be coupled and/or functionally associated with one another, so as to form a complex support structure during deployment, for example, a bifurcated support structure and/or a helical and/or double helix configuration, or the like.

The principles and operation of the present invention may be better understood with reference to the drawings and the accompanying description. The following figure reference characters are used throughout the description to refer to similarly functioning components are used throughout the specification hereinbelow.

10 basic structure;
10a angel;
10o open structure;
10f filament;
10s sigmoidal connecting structure;
50 support structure;
50L long axis;
50s short axis;
50c open crimped configuration;
50e open non-crimped planar configuration;
50f closed non-planar folded configuration;
52 support structure body;
54 locking members;
54c closed/interlocked members;
55 axial support member;
100 prosthetic valve assembly;
100c open crimped configuration;
100e open non-crimped planar configuration;
100f closed non-planar folded configuration;
100o valve outflow end;
100i valve inflow end;
102 valve support structure body;
102c support structure crimped configuration;
104 coupling locking member;
110 valve body;
112, 114, 116 valve leaf;
118 valve annulus;
150 prosthetic atrio-ventricular valve;
150c crimped planar configuration;
150e extended planar configuration;
150f folded configuration;
152 support structure body;
152a upper support structure portion;
152b medial support structure portion;
152c lower support structure portion;
152s sigmoidal connecting member;
154 coupling members;
154a first coupling member;
154b second coupling member;
155 axial support member;

FIG. 1A-D shows the different configurations assumed by the intraluminal support structure 50 according to embodiments of the present invention. Namely, support structure is capable of assuming an open crimped configuration 50c as shown in FIG. 1A, an open non-crimped planar configuration 50e as shown in FIG. 1B, and optional folded configurations 50f in the form of a stent-like tubular structure 200 shown in FIG. 1D, and in the form of a valve-like cylindrical structure 100 shown in FIG. 1C.

FIG. 1A shows schematic illustrative diagram of the open crimped configuration 50c of support structure 50. The open crimped configuration 50c is configured to have a short axis 50s and a long axis 50L. Importantly support structure 50c is flat and/or planar so as to assume minimal dimensions along short axis 50s. Such minimization along the short axis 50s provides the support structure with maneuverability so as to improve its delivery to an anatomical delivery site where it transitions to its final folded configuration 50f, FIG. 1C-D.

The transition from the open non-crimped planar configuration 50e, shown in FIG. 1B, involves crimping across long axis 50L of support structure 50, as shown by the directional arrows.

Accordingly the crimped planar configuration 50c is advantageous in that it allows for improved maneuverability of the support structure 50c within the anatomy during the support structure's delivery.

As previously described this open crimped configuration 50c according to the present invention allows a practitioner to conveniently maneuver the support structure during delivery while further allowing the practitioner to readily urge the device to assume sharp and/or acute angles, particularly through tortuous anatomy. Furthermore, the open crimped configuration 50c provides a profile further enables a practitioner to reduce scarring size and/or signature when penetrating through tissue for example cardiac tissue such as the cardiac septum.

Crimping support structure 50e provides an elongated open crimped configuration, however one that remains sufficiently flexible so as to be able to assume acute angles while being delivered within the anatomy. The longitudinal crimping reduces the width of support structure 50e along short axis 50s by about at least 20% and more preferable up to about 80%, while increasing the length 102L by a factor of up to about 100%. Therefore the delivery configuration has a small short axis 50s that is advantageous in that it is readily maneuverable.

Support structure 50 may take optional forms for example including but not limited to a vessel support structure to maintain vessel patency such as a stent, FIG. 1C, or may be utilized as an orifice for supporting a valve body, FIG. 1D.

Support structures 50 may be provided from optional biocompatible materials for example including but not limited to polymers, alloys, smart materials, shape memory materials, nitinol, materials exhibiting plastic deformation, super-elastic metal alloy which transforms from a austenitic state to a martensitic state, any combination thereof or the like as is known in the art.

In some embodiments at least a portion of support structure 50 may be coated with an agent and/or medicament and/or drug to form a drug eluting support structure, for example as is known in the form of a drug eluting stent.

Support structure 50 is configured to remain in the open crimped configuration 50c during both the introduction (into the anatomy) until reaching the implantation and/or placement site. During deployment at the implantation site, support structure 50c is configured to transition and/or transform into its folded configuration 50f for example assuming a stent-like shape, FIG. 1C, or valve-like shape, FIG. 1D, at the implantation site. Accordingly, as the open crimped support structure 50c is delivered into the implantation anatomy it begins to expand so as to assume its final folded configuration 50f.

In embodiments the folded configuration 50f may be configured to assume a variety of optional configuration for example including but not limited to any structural geometric shape, curvilinear shape, folded shape, open folded shape, closed folded shape, cylindrical, bifurcated, furcated, trapezoidal cylinder, curvilinear, tertiary structure, secondary structure helical, double helix, looped, lobular, ellipsoid, ovoid, paraboloid, vortex, hyperboloid, hyperbola, parabola, conical section, toroidal, sigmoidal, multi-loop, solenoidal, any combination thereof or the like.

During transformation and/or transitioning support structure 50c, may undergo a progressive unfolding and/or unraveling and folding process including expansion, rotation, and torsion, along short axis 50s and/or long axis 50L so as to assume its final shape 50f within the anatomical implantation site.

Support structure 50 may be expanded from its crimped configuration along its long axis 50L in a rotated or torsade manner around a central axis in order to obtain its work configuration with a curvilinear or the like folded and/or circular structure.

In some embodiments a plurality of crimped support structures 50c may be transformed substantially simultaneously so as to combine to form a final complex structural configuration, for example including but not limited to a bifurcated support structure or the like, not shown.

The transformation form a planar crimped support structure 50c to the folded configuration 50f of support structure 50 is provided at the anatomical delivery site. The transformation may be provided by controlling the transformation conditions at the delivery site. For example, the transformation may be triggered and/or initiated in response to exposure to a triggering agent and/or signal for example including but not limited to a temperature change, either an increase and/or a decrease. A transformation triggering agents and/or signal may for example include but is not limited to at least one or more, or a combination of selected from: temperature change, chemical agent, electromagnetic field, electromagnetic current, acoustic signal, optical signal, magnetic field, the like as is known in the art or any combination thereof.

Preferably following and/or during the final stages of the transformation phase the planar crimped structure is closed and interlocked and/or folded and/or overlapping onto itself to define a closed structure 50f along at least one of a short side 50s, a long side 50L, or a combination thereof.

In embodiments support structure 50 may comprise at least one or more coupling and/or locking members 54 that provided for folding and/or closing the support structure to its closed folded configuration 50f. In embodiments locking members 54 may be located along any portion of support structure 50 for example including but not limited to short axis 50s, long axis 50L, support structure body 52, or any combination thereof.

In some embodiments support structure 50 may comprise two or more coupling and/or locking members 54 that are provided in optional forms and configured to correspond and/or lock with one another. Optionally the two or more coupling member may correspond to one another.

In embodiments locking members 54 may be coupled with one another with the aid of a dedicated tool, for provided in optional forms for example including but not limited to plyers, leads, guidewire, leading wires, threading wire, the like or any combination thereof.

In embodiments corresponding locking member 54 may be coupled to form an interlocked and/or closed coupling member 54c, for example as shown in FIG. 1C-D.

In embodiments locking members may be provided in optional forms for example including but not limited to pin and hooks, male/female couplers, peg and recess, latch and buckle, sutures, hook and loop, wire the like or any combination thereof.

In embodiments couplers 54 may optionally be provided in the form of a biocompatible adhesives and/or cement that may be cured during deployment process.

In some embodiments support structure 50 may be provided in the form of a substantially rectangular configuration having opposing long edges along long axis 50L and opposing short edge along short axis 50s, that define a support structure body 52. The support structure body 52 is formed from a plurality filaments 10, shown in FIG. 1E-G. Support structure is not limited to a rectangular configuration as shown here it may assume any shape.

Support structure body 52 is provided from a plurality of basic structures 10, FIG. 1E-G, that form of a braided scaffold structure of filaments 10f defining a plurality of interlinking points 10i that form a rhomboid recess 10o. The interlinked filaments forming recess 10o along an intersection point 10i provides the necessary flexibility of support structure 50 and the capability of assuming the various configuration of support structure including open crimped configuration 50c, folded 50f, and open non-crimped planar 50e, as shown in FIG. 1A-D.

In embodiments, the basic structure 10 provides support member 50 with the ability to control and assume the different configurations by crimping along at least one dimension of the support structure body 52, either along its long side 52L or short side 52s. Accordingly controlling the relative position of filaments 10 relative to one another allows body 52 to assume the smaller open crimped configuration 50c prior to introduction into a delivery sheath and/or device, for example a catheter (not shown); or to assume the larger configuration in the form of an open non-crimped planar configuration 50e, and finally a folded configuration 100f during deployment at the implantation site following a transition phase.

FIG. 1E-G show the basic units 10 that may be utilized to form a support structure 50 is formed from a plurality of filaments 10f, arranged at an angle 10a relative to one another forming an intersection 10i defining an opening 10o.

In some embodiments, opening 10o may assume a polygonal shape, FIG. 1E, resembling at least one or more of a parallelogram, a rhombus, a regular rhomboid, an irregular rhomboid, or the like polygon or quadrilateral. In some embodiments opening 10o may assume a closed curvilinear configuration, FIG. 1F, resembling a circle, ovoid, ellipsoid, circular like structure, or the like closed curvilinear structure.

More preferably support structure is configured such that the angle 10a formed at filament intersection 10i is controllable to determine the dimensions of the support structure 50.

In some embodiments, as shown in FIG. 1G, filament intersection 10i may be provided in the form of a sigmoidal connecting structure 10s, as shown. Such a sigmoidal connecting structure 10s renders additional flexibility along the long axis 50L therein allowing the intersection to be stretched and condensed in the long axis 50L controlling the shape and size of structure 50.

Support structure flexibility is obtained from its structure comprising a plurality of angled intersections wherein the intersection angle 10a, is controllable in that it may be changed when transitioning between the crimped planar 50c and the open non-crimped planar 50e configurations or vice versa.

In embodiments the polygonal recess 10o may be distributed in any manner along support structure 50 to form a desired configuration of support structure 50.

In embodiments support structure 50 may be provided from a sheet material that is laser cut to assume the support structure configuration, defining a plurality of polygonal recess 10.

In embodiments support structure 50 may be provided by way of braiding and/or weaving of a plurality of filaments 10f to form the support structure. During the braiding of a plurality of filaments the angles formed between filaments may be controlled so as to form the desired polygonal intersecting structure.

In embodiments the size of basic structure 10 is controllable so as to allow it to assume a planar crimped configuration 50c having minimal short dimension (FIG. 1A), or open non-crimped planar configuration 50e having maximal short dimension (FIG. 1B).

In embodiments, the support structure 50 comprising a plurality of polygon frame structures 10 is expandable in its long axis in a linear, rotated or torsade manner around a central axis in order to obtain its work configuration with a circular shape.

In some embodiments support structure body 52 may optionally further feature at least one or more axial support member 55, an example of which is shown in FIG. 1A. Axial support member 55 provides a longitudinal axis and/or anchor point along the long dimension 50L of body 52. Axial support member 55 may be provided in the form of a continuous flexible sheet utilized to increase the strength of folded configuration 50f by providing an anchoring axis while retaining the flexibility of the planar-crimped configuration 50c. Axial support member 55 may feature a locking member 54 at an end thereof, as described in greater detail with respect to FIG. 6A-D.

FIG. 2A shows a perspective side view of an intraluminal support structure in the form of a prosthetic valve 100 according to embodiments of the present invention. FIG. 2A shows the prosthetic valve 100 in its final deployed configuration as it would be deployed within the required anatomy, for example including but not limited to the heart so as to replace a cardiac valve.

Prosthetic valve 100 includes a cylindrical support structure 102 that is fit with a valve body 110.

In embodiments valve body 110 may comprise at least two or more leaflets 112, 114, 116. Valve body 110 is a provided from prosthetic valve tissue or tissue like membrane that may be made of variable biocompatible materials for example including but not limited to biological tissue, biological matter, engineered materials, grown materials, transplanted tissue, biocompatible polymeric materials, the like materials or any combination thereof.

In embodiments valve body 110 may be configured in terms of sizing, shape, number of leaflets, according to at least one valve parameter for example including but not limited to the intended anatomy, the implantation site, form and function of the prosthetic valve, or any combination thereof.

Support structure 102 forms a cylindrical body having a radius and height that are configured according to the intended form and function of the prosthetic valve 100. Sizing of the support structure is accordingly adjusted and/or configured according to the intended anatomy, implantation site, form and function of the prosthetic valve, or any combination thereof.

FIG. 2A-E show support structure 100 in its final deployed and folded form 100f. Accordingly, in its final folded form 100f support structure 102 defines a cylindrical body formed from a support structure that has folded over itself over a short edge and coupled along corresponding short ends. As shown, the short edge of support structure 102 overlap over corresponding locking members 104 so as to form the folded cylindrical structure 100f.

Locking members 104 are utilized to form the cylindrical shape of prosthetic valve body 100. Folding of support structure provides for forming overlapping portions of the support structure 102, for example along its short axis 102s or long axis 102L, shown in FIG. 3A. Such overlapping may be configured to allow for locking and/or closing the support structure with locking members 104 enabling support structure to assume its final folded shape configuration 100f.

The support structures 102 in its working folded configuration defines an inflow end 100i, shown in FIG. 2B-C, and an outflow end 100o, shown in FIG. 2D-E.

Most preferably during deployment with the necessary tools the support structure 102 expands from the open crimped configuration 100c, utilized during introduction and delivery as shown in FIG. 4, to assume the folded circular shape 100f, as shown in FIG. 2A-E.

Once folded placed and functionally integrated within the appropriate anatomical structure, valve 100 is rendered functional wherein valve body 110 to ensures a one-way fluid direction from the inflow end 100i, FIG. 2B-C, to the outflow end 100o, FIG. 2D-E.

FIG. 2B shows a top down view of the proximal surface of the prosthetic valve 100 revealing the commissural juncture of valve body 110, exemplarily shown in the form of a three leaflet valve utilizing leaflets 112, 114, 116, therein defining the inflow end 100i, forming a prosthetic tricuspid valve.

FIG. 2C shows a perspective top down view of the prosthetic valve assembly 100 depicted in FIG. 2B, therein showing the inflow end 100i.

FIG. 2D shows a perspective bottom up view of the distal surface of the prosthetic valve 100, revealing the outflow end 100o.

FIG. 2E shows a perspective side view of valve assembly 100, further showing the valve body formation.

Figure 7:
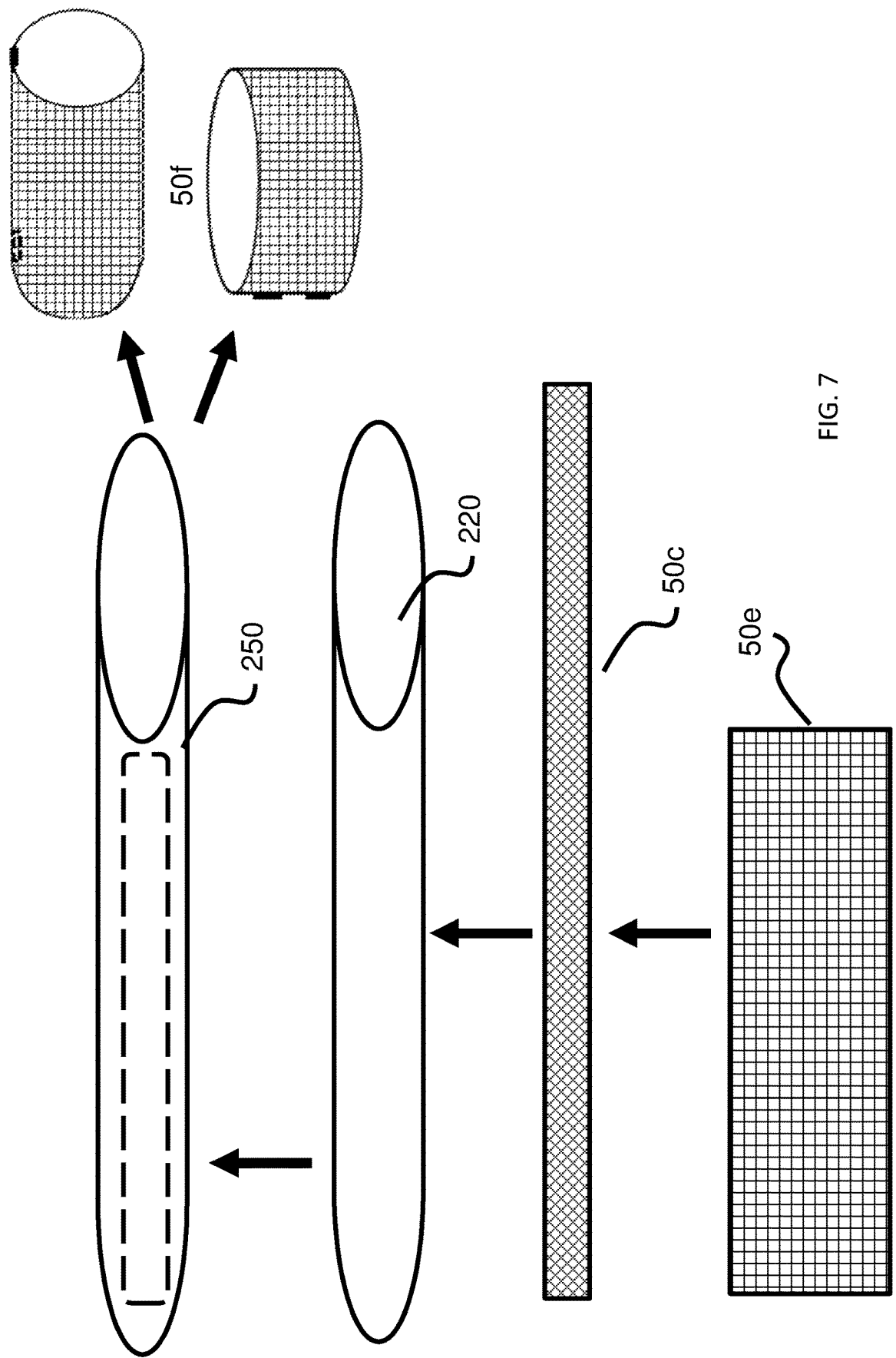
FIG. 7 shows a schematic illustration of a delivery system for the support structure according to embodiments of the present invention.

FIG. 3A-E show various views of prosthetic valve 100 in the open non-crimped planar configuration 100e showing an expanded configuration. The expanded/non-crimped configuration 100e depicts the pre-crimped configuration of valve 100, prior to crimping in preparation for introduction and delivery within the anatomy. Most preferably crimping of open non-crimped planar configuration 100e is provided with dedicated process and tools so as to allow placement of valve 100 into a delivery system 250 for example utilizing a catheter and/or sheath 220, as schematically shown in FIG. 7.

In some embodiments the fully open non-crimped planar configuration 100e may be used during deployment within the anatomical implantation site. More preferably, during deployment of valve 100 is configured to transition from the open crimped configuration 100c to the folded configuration 100f wherein the open non-crimped planar configuration 100e is a temporary and/or gradual transitional phase for portion of the valve body 102 such that the fully open non-crimped planar configuration 100e, as shown, is not necessarily realized within the implantation site.

In embodiments the open non-crimped planar configuration 100e may be assume the folded configuration 100f by optional means and/or tools for example including but not limited to folding, rotation, torsion, and/or overlapping along a short axis 102s. The open non-crimped planar configuration 100e as shown in FIG. 3A-E are shown here for illustrative purposes only as preferably it is not a state that is maintained for an extended period of time within the anatomy. Preferably within the implantation site anatomy the transformation and/or transition from a crimped planar configuration 100c, FIG. 4, to the folded final configuration, 100f as shown in FIG. 2A, takes place in an efficient manner such that the transition phase, for example including but not limited to folding, torsion occurs, simultaneously during the transformation process, such that the fully open non-crimped planar configuration of the vessel support structure is in its largest expanded dimensions is generally not exhibited within the anatomy.

In some embodiments the vessel support structure may be delivered and/or placed within the implantation site in an open non-crimped planar configuration 100e.

FIG. 3A shows the internal surface of valve assembly 100 that is fit with a valve body 110 showing individual valve leaflets 112, 114, 116 of and valve annulus 118 that form valve body 110 that is featured along the open non-crimped planar surface 100e of support structure 102.

In embodiments, valve body 110 is associated with and/or coupled with support structure 102 to form prosthetic valve 100, in a manner as is known and accepted in the art for example including but not limited to suturing, biocompatible adhesives, mounting clips, couplers, any combination thereof or the like as is known in the art.

FIG. 3B shows an external surface view of valve assembly 100 that shows the support structure 102 and coupling members 104. Coupling members 104 are utilized to form the folded structure valve assembly 100f so as to provide a cylindrical conformation 100f from the planar conformation 100e, 100c by way of folding over short edges and utilizing coupling members 104 to lock short edges. Coupling members 104 are shown in an optional configuration herein depicted in the non-limiting form of pegs that may be manipulated to interlock the short ends 102s of support structure 102.

Embodiments of the present invention are not limited to this form of coupling and/or locking members and may be provided in any form for example including but not limited to male/female couplers, peg and recess, latch and buckle, sutures, hook and loop, wires, corresponding threading, the like or any combination thereof.

In embodiments locking members 104 may be locked with the aid of a dedicated tool, provided in optional forms, for example including but not limited to plyers, leads, guidewire, leading wires, threading wire, the like or any combination thereof.

In embodiments coupling member 104 may be provided from dedicated smart materials, shape memory materials that are configured to undergo a specific transition to assume the locked configuration when exposed to transitioning conditions and or elements during the deployment process.

In embodiments couplers 104 may optionally be provided in the form of a biocompatible adhesives and/or cement that may be cured during deployment process.

Optionally coupling members 104 may be provided in the form of pin and hooks so as to allow for the overlapping extremity to form an overlapping tight and stable seal between overlapping edges, for example as shown in FIG. 2A.

Optionally support structure 100 may comprise two or more coupling and/or locking members 104 that are provided in optional forms and configured to correspond and/or lock with one another.

FIG. 3A shows a face on view from the short end 102s showing a leaflet 112, 114, 116 and annulus 118 of valve body 110 as extending away from support structure 102. FIG. 3C shows an end view of valve 100 showing the placement of valve body 110 relative to support structure 102.

FIG. 3D shows a face on view of external surface of valve assembly 100 similar to the depicted in FIG. 3B.

FIG. 3E shows a perspective view along the long edge 102L of support structure 102

FIG. 4 shows schematic diagram of the crimped-planar configuration 100c of support structure 100 where for illustrative purposes valve body 110 is removed. As shown, support structure 102 in its open crimped configuration 100c is provided in the form of a support structure having a minimal dimension along the short end of axis 102s. The transition from the open non-crimped planar configuration 100e, shown in FIG. 3B, involves crimping across opposing long edges of long axis 102L of support structure 102, as shown by the directional arrows. Such crimping provides a long configuration however one that remains sufficiently flexible so as to be able to assume an acute angle while being introduced within the anatomy. The longitudinal crimping reduces the width of support structure 102 along short edge of short axis 102s by about at least 20% and more preferable up to about 80%, while increasing the length of axis 102L by a factor of up to about 100%. Therefore the delivery configuration has a small short edge along axis 102s that is advantageous in that it is readily maneuverable in tortuous anatomy and has a small scar size and/or signature when penetrating through cardiac tissue for example including but not limited to cardiac septum.

FIG. 5A-B show various view support structure 102 that is folded assuming its final configuration in the form of a stent. Structure 102 is shown where is folded over the short edge of axis 102s, however it may similarly be folded along its long edge of axis 102L.

FIG. 5B shows two short edges of axis 102s that are interlocked over locking members 104. The location of locking members may be controlled in order to determine the final structural shape of support structure 102.

Figure 6C:
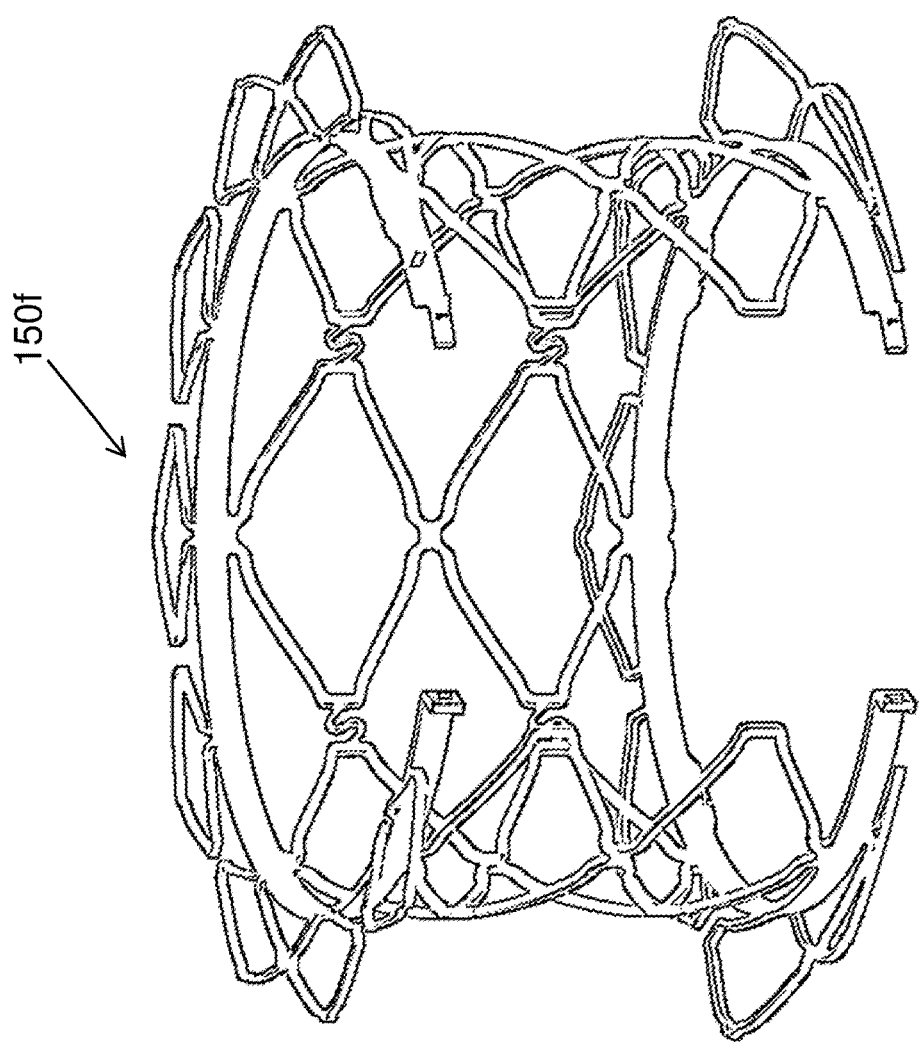

FIG. 6A-D shows an optional embodiment for a prosthetic valve support structure 150 featuring an axial support member 155. Axial support member preferably provides additional structural integrity and strength along the length of valve 150 while maintaining both maneuverability and flexibility of the overall structure 150. In embodiments axial support member 155 may be provided from a valve support structure 150 includes two axial support members 155 are disposed along the long axis 150L. FIG. 6A shows an open crimped configuration 150c. FIG. 6B shows an open non-crimped planar configuration 150e. FIG. 6C shows an open configuration of a partially folded configuration 150f of valve 150

The two axial support members define three sub segments of support structure body 152 including an upper portion 152a, a medial portion 152b and a lower portion 152c.

In embodiments upper portion 152a may be formed from a plurality of basic structures 10 extending above a first axial support member 155a. In an optional embodiment each basic structure 10 of upper portion 152a may be individually connected to and extending from the first axial support member 155a. In an optional embodiment a plurality of basic structure 10 may be interconnected with one another and collectively extend from first axial support member 155a, so as to form upper portion 152a. In embodiments interconnected basic structures 10 may be coupled and/or associated with one another utilizing a sigmoidal connecting member 152s.

In embodiments lower portion 152c may be formed from a plurality of basic structures 10 extending below a second axial support member 155b. In an optional embodiment each basic structure 10 of lower portion 152c may be individually connected to and extend from second axial support member 155b. In an optional embodiment a plurality of basic structure 10 may be interconnected with one another and collectively extend from second axial support member 155b, so as to form lower portion 152c. In embodiments interconnected basic structures 10 may be coupled and/or associated with one another utilizing a sigmoidal connecting member 152s, for example as shown.

In embodiments medial portion 152b may be formed from a plurality of interconnected basic structures 10 disposed between a first axial support member 155a and a second axial support member 155b, therein connecting both axial support members 155. In embodiments interconnected basic structures 10 may be coupled and/or associated with one another utilizing a sigmoidal connecting member 152s, for example as shown.

In embodiments each support structure portion 152a,b,c may be individually crimped to assume an open crimped configuration.

In embodiments each support structure portion 152a,b,c may be individually un-crimped to assume an open non-crimped planar and/or folded configurations.

In embodiments medial portion 152b is preferably crimped to assume a crimped planar configuration as previously described, for example as shown in FIG. 6A. The open crimped configuration may be achieved by crimping along short axis so as to urge axial support members 155 toward one another, as is depicted by the directional arrow. FIG. 6B shows the open non-crimped planar configuration 150e where medial portion 152b is extended as shown with directional arrow wherein support members 155a,b are extended away from one another.

FIG. 6C shows as folded configuration 150f of prosthetic valve support structure 150 in an open configuration, as it would appear following deployment in the implantation site anatomy and prior to closure of the prosthetic valve utilizing corresponding locking members 154, so as to form the closed valve structure (no shown).

In embodiments support member 155 may optionally and preferably feature a locking member 154 along an end thereof, for example as shown. FIG. 6A-D shows a close up view of optional locking members 154 provided in the form of a male latch member 154a and female buckle member 154b configuration. As previously described locking members may be provided in a plurality of optional forms.

In some embodiments locking members 154 may be coupled with one another with the aid of a dedicated tool, provided in optional forms for example including but not limited to plyers, leads, guidewire, leading wires, threading wire, the like or any combination thereof.

FIG. 7 shows a schematic illustration of the process of delivering and deploying the support structure 50, 100, 150 as previously described, that is delivered with a delivery sheath and/or catheter 220 once loaded forming a delivery catheter 250. An additional advantage of the support structure according to the present invention is that a single delivery system, for example a catheter and/or sheath 250 may be utilized for a plurality of optional support structures having variable diameters and/or sizes. That is because the final shape of the folded configuration 50f has no bearing on the delivery system. This is an improvement over the state of the art delivery systems that must be specific relative to the size of the support structure being delivered.

Accordingly embodiment of the present invention provide for use of a single delivery system irrespective of the final diameter and/or size of the support structure being delivered this is specifically due to the crimping along the short axis as previously described.

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

It should be noted that where reference numerals appear in the claims, such numerals are included solely or the purpose of improving the intelligibility of the claims and are no way limiting on the scope of the claims.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

While the invention has been described with respect to a limited number of embodiments, it will be appreciated that many variations, modifications and other applications of the invention may be made.

What is claimed is:

1. A system for introducing an intraluminal support structure to a patient's body for implantation at a delivery site or implantation site, said system comprising:
   (1) an intraluminal support structure having a body capable of transitioning between three configurations including:
   a) an open non-crimped planar configuration having a length along a long axis and a width along a short axis;
   b) an open crimped planar configuration wherein the length has been elongated and the width has been reduced; and
   c) a closed non-planar folded configuration;
   wherein the body in its open non-crimped planar configuration is configured to be stretched in a long axial direction to transition said body to form said open crimped configuration and to provide said body with a minimal short axis and a maximal long axis therein providing said open crimped configuration with increased flexibility; and
   (2) a delivery carrier member in the form of a catheter or sheath defining a delivery system utilized for introducing said support structure to a body for implantation at a delivery site or implantation site; and
   wherein said open crimped configuration is controllably disassociated from said delivery system to be deployed at said delivery site, and wherein during deployment said open crimped configuration transitions to assume said closed non-planar folded configuration, wherein said transition is established by way of at least one of expansion, torsion or folding and wherein said closed non-planar folded configuration is finalized by closing said body by interlocking an end thereof along one of said long axis or said short axis.

2. The system of claim 1 wherein said closed non-planar folded configuration is closed by overlapping and interlocking portions of said body along one of said long axis or said short axis.

3. The system of claim 1 wherein said support structure body is provided from an arrangement of a plurality of filaments forming a planar scaffold, and wherein said filaments form a interlinking points defining an interlinking angle at said interlinking point that define a planar opening formed from at least two opposing interlinking points, characterized in that said support structure is configured to transition between said open non-crimped planar configuration to said crimped configuration by adjusting said interlinking angle.

4. The system of claim 3 wherein said filaments are arranged by one of braiding, weaving, interlacing, or any combination thereof.

5. The system of claim 3 wherein said interlinking angle controls the length of at least one said long axis or short axis.

6. The system of claim 3 wherein said planar opening is provided with a shape selected from the group consisting of a polygon, a parallelogram, a rhombus, a regular rhomboid, an irregular rhomboid, a quadrilateral.

7. The system of claim 3 wherein said planar opening assumes a planar closed curvilinear contour.

8. The system of claim 7 wherein said curvilinear contour is selected from a circle, ovoid, ellipsoid, circular, hyperboloid, parabolic, conical, sigmoidal, and any combination thereof.

9. The system of claim 3 wherein said filament intersection further features a connecting filament member.

10. The system of claim 9 wherein said connecting filament member is shaped to be a sigmoidal connecting structure.

11. The system of claim 1 wherein said support structure body further comprises at least one axial support member along at least a portion of the length of said body along said long axis.

12. The system of claim 11 wherein said axial support member is disposed between two opposing long edges of said long axis.

13. The system of claim 11 having at least two axial support members forming an upper portion, medial portion, and lower portion along said support structure body.

14. The system of claim 11 wherein said axial support member is formed from a continuous flexible sheet.

15. The system of claim 11 further comprising corresponding locking members disposed at each end of said axial support member.

16. The system of claim 1 wherein said support structure body is formed from biocompatible materials selected from a group consisting of polymers, alloys, smart materials, shape memory materials, shape memory alloys, shape memory polymers, nitinol, materials exhibiting plastic deformation, super-elastic metal alloy which transforms from an austenitic state to a martensitic state and any combination thereof.

17. The system of claim 1 wherein said support structure body is formed from smart materials or shape memory materials that are configured to undergo a specific shape transition from the open crimped configuration to the closed non-planar folded configuration by applying a transition triggering condition or agent selected from temperature change, application of electromagnetic field, application of a magnetic field, application of electrical current, exposure to a specific electromagnetic wavelength, exposure to a biocompatible material, exposure to a chemical agent, exposure to a biological agent, application of an acoustic signal, application of an optical signal, any combination thereof.

18. The system of claim 1 wherein said closed non-planar folded configuration is selected from cylindrical, bifurcated, furcated, trapezoidal cylinder, curvilinear, tertiary structure, secondary structure helical, double helix, looped, lobular, ellipsoid, ovoid, paraboloid, vortex, hyperboloid, hyperbola, parabola, conical section, toroidal, sigmoidal, multi-loop, solenoidal, any combination thereof.

19. The system of claim 1 wherein said closed non-planar folded configuration comprises a plurality of crimped support structures that are combined with one another during deployment.

20. The system of claim 1 further comprising at least one locking member.

21. The system of claim 20 wherein said locking members are disposed along any portion of support structure.

22. The system of claim 20 wherein said locking members comprise pin and hooks, male female couplers, peg and recess, latch and buckle, sutures, wire, corresponding threading, hook and loop, or any combination thereof.

23. The system of claim 20 wherein said locking members comprise sutures, biocompatible adhesives, biocompatible cements, curing agents, any combination thereof.

24. The system of claim 20 wherein said locking members are configured to be manipulated with a tool selected from a group consisting of plyers, leads, guidewires, leading wires, threading wires, and any combination thereof.

25. The system of claim 1 wherein said support structure body further comprises a valve body defining a prosthetic valve (100, 150) and wherein said valve body is configured to form a prosthetic valve in the form selected from semilunar valve, pulmonary valve, aortic valve, atrioventricular valve (AV valve), mitral valve, bicuspid valve, tricuspid valve, sphincter, cervix.

26. The system of claim 25 wherein said valve body is formed from materials selected from biological tissue, biological matter, engineered materials, grown materials, transplanted tissue, biocompatible polymeric materials, and any combination thereof.

27. The system of claim 1 wherein at least a portion of support structure may be coated with at least one or more selected from the group consisting of an agent, a medicament, a drug, an eluting medicament, a controlled release medicament, a controlled release agent, any combination thereof.

28. The system of claim 1 wherein the length of said short axis is reduced by at least 20% and up to about 80% when transitioning between said open non-crimped planar configuration and said crimped configuration.

29. The system of claim 1 wherein the length of said long axis increases by a factor of up to about 100% when transitioning between said open non-crimped planar configuration and said open crimped configuration.

* * * * *